(12) United States Patent
Arnold

(10) Patent No.: US 6,220,725 B1
(45) Date of Patent: Apr. 24, 2001

(54) INTEGRATING CAVITY LIGHT SOURCE

(75) Inventor: Stephen C. Arnold, Honeoye Falls, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/050,439

(22) Filed: Mar. 30, 1998

(51) Int. Cl.[7] .................................................. F21V 1/00
(52) U.S. Cl. ........................ 362/241; 362/238; 362/800
(58) Field of Search .................................. 362/227, 231, 362/249, 247, 800, 241, 238; 355/70; 399/4, 5; 358/474, 494, 509, 483; 350/341.7; 257/98, 99, 100; 377/63

(56) References Cited

U.S. PATENT DOCUMENTS

| | | |
|---|---|---|
| 5,442,533 * | 8/1995 | Kaplan ................................ 362/303 |
| 5,490,048 * | 2/1996 | Brassier ............................... 362/238 |
| 5,548,120 | 8/1996 | Parker et al. . |
| 5,785,418 * | 10/1997 | Hochstein ............................ 362/373 |
| 5,898,510 * | 2/1998 | Kaihotsu .............................. 358/509 |
| 5,902,993 * | 12/1996 | Okushiba .......................... 250/208.1 |

* cited by examiner

*Primary Examiner*—Sandra O'Shea
*Assistant Examiner*—Peggy A Neils
(74) *Attorney, Agent, or Firm*—Svetlana Z. Short; William J. Greener

(57) ABSTRACT

A light source device includes a housing forming a cavity with a diffusely light reflective interior surface and an exit port; at least one LED on the interior surface; a light reflective layer and an electrically and thermally conductive layer between the LED and the housing; electrical contacts interconnecting the LED and the outside of the housing, such that electrical power applied to the contacts causes the LED to emit light.

25 Claims, 16 Drawing Sheets

INTEGRATING CAVITY LIGHT SOURCE

CROSS REFERENCE TO RELATED APPLICATIONS

This application is related to the following concurrently filed application Ser. No. 09/020,611, entitled A LIGHT SOURCE, in the name of Stephen C. Arnold.

FIELD OF THE INVENTION

This invention relates to integrating cavities and more particularly to integrating cavities utilizing Light Emitting Diodes as light sources.

BACKGROUND OF THE INVENTION

Integrating cavities are known. Integrating cavities are typically made with a spherical housing having diffusely reflective (95–100% reflectivity) inner walls. An intense beam of light (infrared, visible, or ultraviolet) is usually introduced into the integrating cavity through an input port. A typical input port is a hole or a slit formed in the housing. Such a hole or a slit becomes a defacto source of light that is being integrated by an integrating cavity. The light is diffusely reflected many times by the interior surfaces of the integrating cavity and is finally emitted through a small exit port of the integrating cavity. A typical exit port is a small hole or a narrow slit formed in the housing.

Integrating cavities are relatively bulky because they have a large, internal cross section (approximately 12 mm or more in diameter), making apparatii that incorporate such integrating cavities also large. The large cross section corresponds to a large (relative to the exit port area) total internal area of the integrating cavity and results in low efficiency (<30%) of the integrating cavity. Efficiency is defined as the ratio of the amount of light exiting the integrating cavity to the amount of light entering the integrating cavity.

Further, for an integrating cavity with a given size total port area (input port area(s) plus exit port area), the larger the input port, the smaller is the efficiency of the integrating cavity. Thus, low efficiency also results when thermal radiation light sources (for example, tungsten filament lamps) or discharge type light sources (for example, xenon, metal halide discharge, or fluorescent lamps) are used to produce the desired beam of light. This is because these light sources are operated external to the integrating cavity, and thus require a large input port.

Individual LED elements and LED arrays can be used to illuminate an integrating cavity. U.S. Pat. No. 5,548,120 discloses an LED array with its LEDs facing into an input port (which is a slit in a housing of the integrating cavity). It also discloses that a plurality of holes could be made in the housing and the individual LEDs can then be placed to face into these holes. The integrating cavities disclosed in this patent have a large circular cross section (relative to array width) and are, therefore, quite bulky. Further, each integrating cavity configuration must be individually determined to efficiently mount a particular LED array internal to the integrating cavity. This must be done in such a way that the LED array assembly does not absorb light, because light absorption reduces the efficiency and brightness uniformity of the integrating cavity. The problems are compounded if LEDs of various wavelengths are required to achieve a specific color balance. This is because these LEDs of various wavelengths often come in different packages, thus requiring a different assembly for LED packages of different wavelength. This renders the optimum mounting of these devices in an integrating cavity very difficult and expensive.

SUMMARY OF INVENTION

According to a present invention, a light source device includes a housing forming a cavity with a diffusely light reflective interior surface and an exit port; at least one LED on the interior surface; a light reflective layer and an electrically and thermally conductive layer between the LED and the housing; electrical contact interconnecting the LED and the outside of the housing, such that electrical power applied to the contacts causes the LED to emit light.

BRIEF DESCRIPTION OF THE FIGURES

The forgoing objects, features, and advantages, of the invention as well as presently preferred embodiments thereof, will become more apparent from reading the following description in connection with the accompanying drawings.

DETAILED DESCRIPTION OF EMBODIMENTS

LED Modules

An LED module includes an LED, at least two electrical connectors attached to the LED, a housing with a first connective feature of a predetermined shape, and a second connective feature of a complimentary shape so that when two LED modules are connected, the first connective feature of the LED module engages a second connective feature of another LED module, preventing relative motion of one LED module with respect to another LED module. A plurality of modules may be assembled into an LED array. The LED array can then be connected to a circuit board via the electrical connectors. An individual LED module may also be attached to a circuit board by the electrical connectors.

Figure 1A:
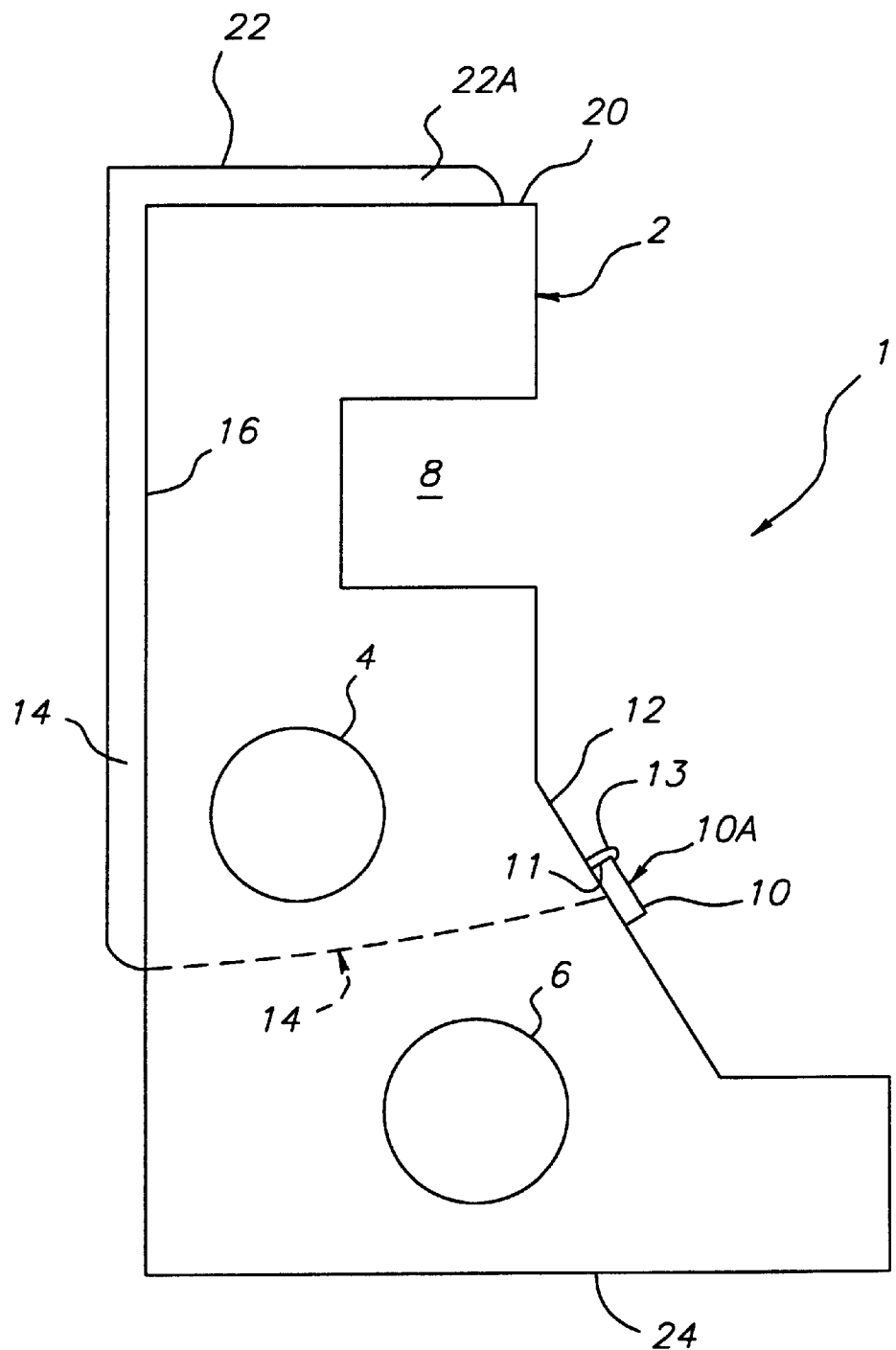
FIG. 1A is a side view of an LED module with snaps.

FIG. 1A shows a side view of an LED module 1 of the first embodiment of the present invention. The LED module 1 comprises a housing 2 with a plurality of connective features in the form of male snaps 4 and female snaps 6, and an optional slot 8. The function of the slot 8 is described in the "Integrating Cavity" section of the specification.

Figure 1B:
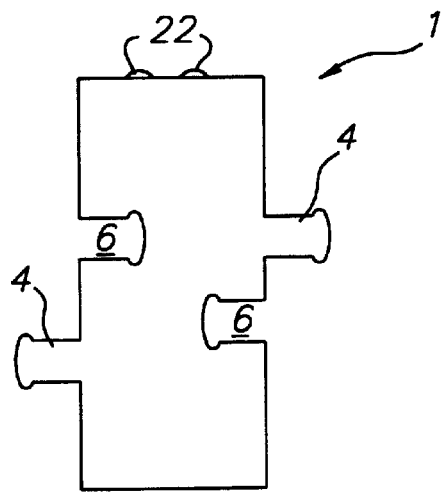
FIG. 1B schematically illustrates a cross section of the LED module of FIG. 1A.
Figure 2:
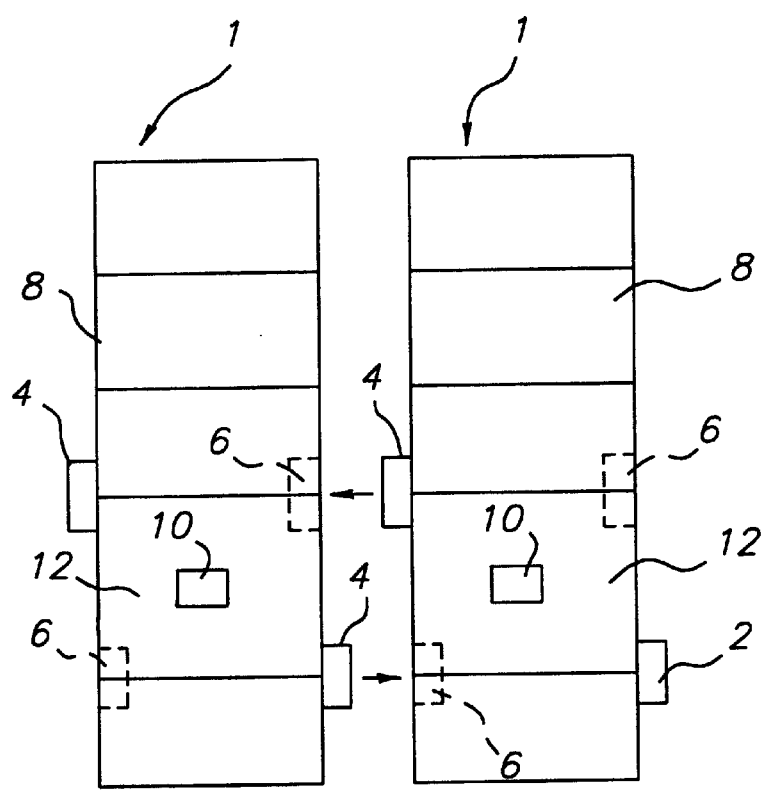
FIG. 2 is a front view of two adjacent LED modules of FIG. 1A with a plurality of mating connective features aligned to one another.
Figure 3:
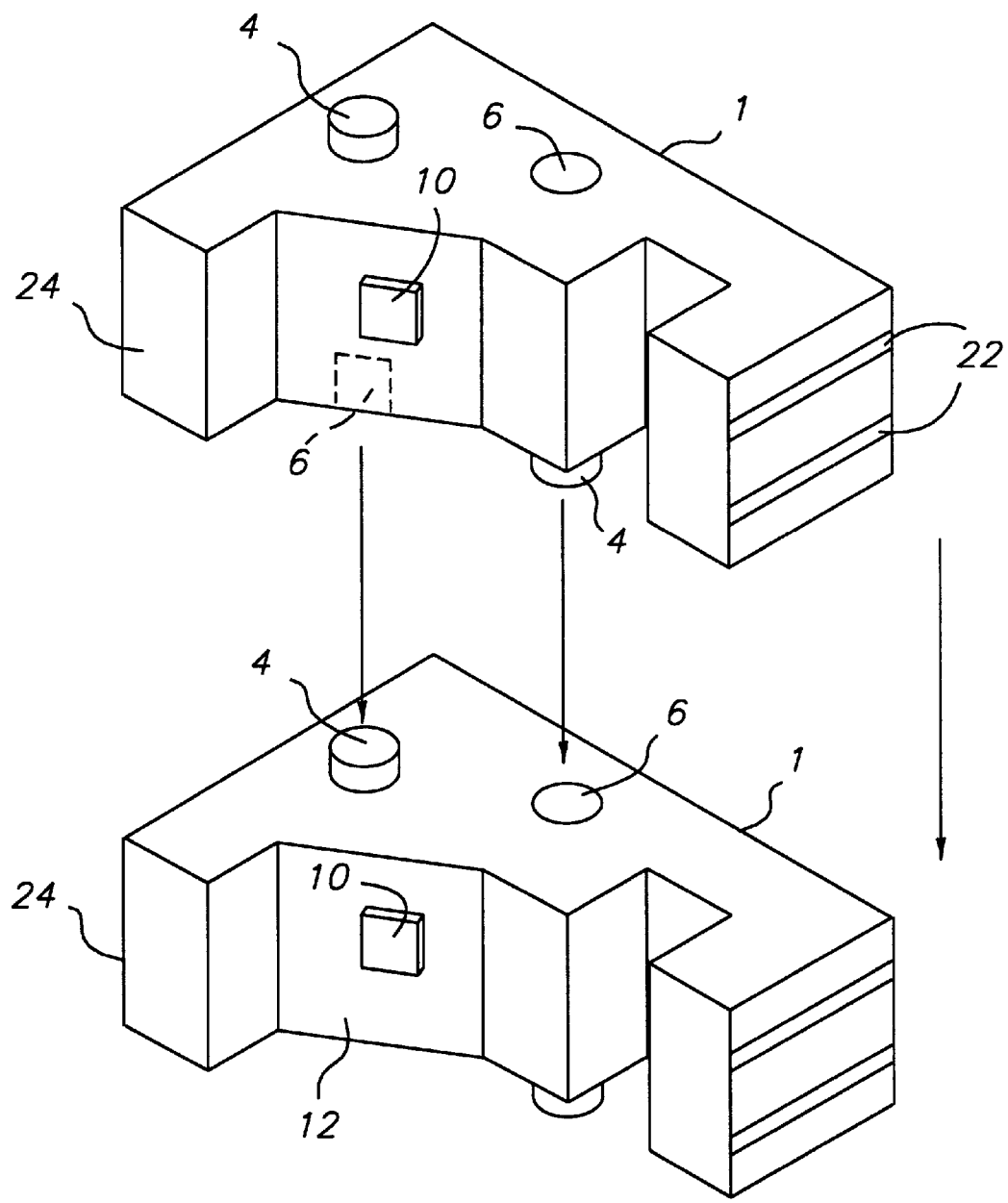
FIG. 3 is a perspective view of the two LED modules of FIG. 2.
Figure 4:
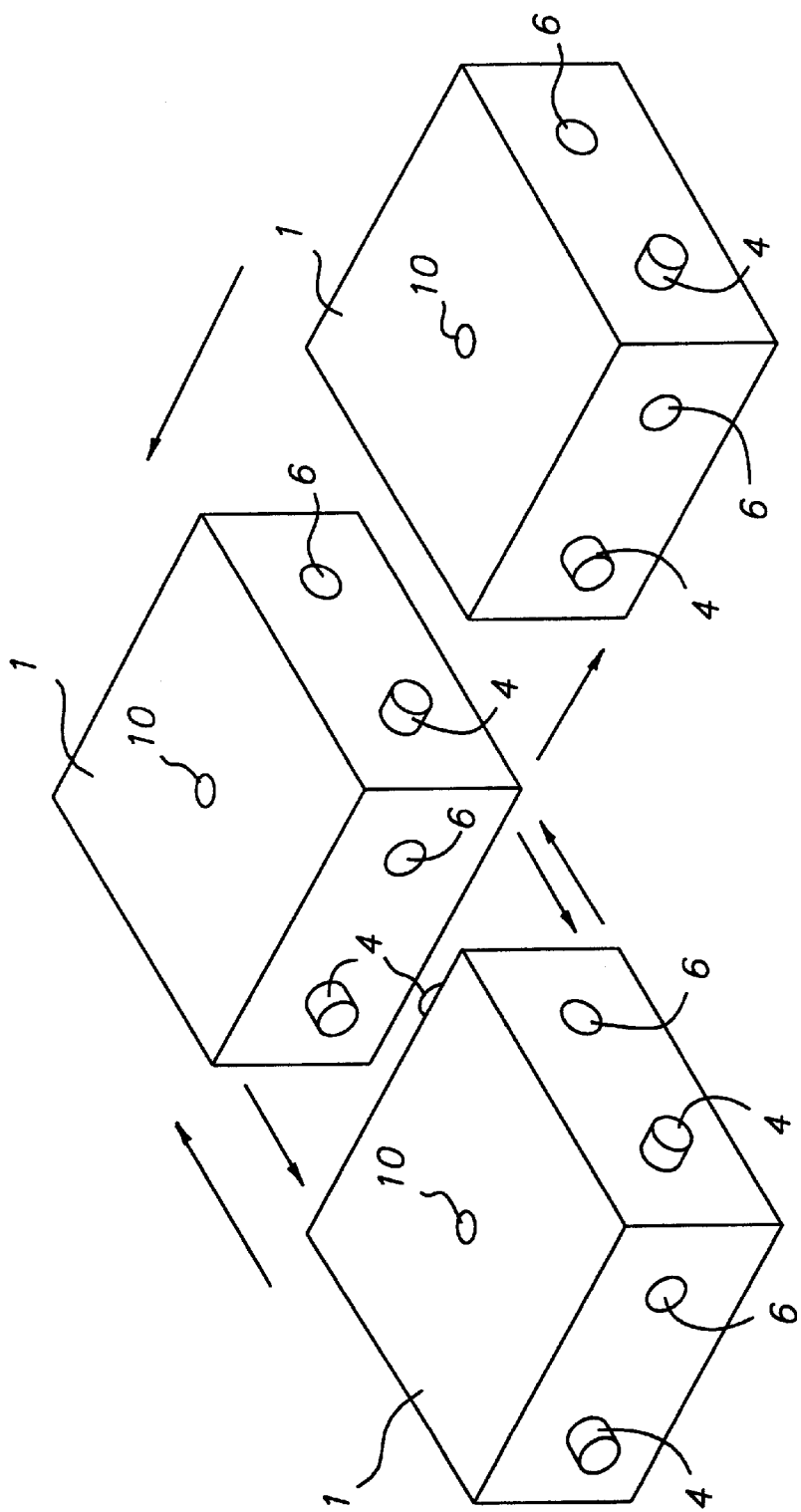
FIG. 4 is a perspective view of three adjacent LED modules arranged to form a two dimensional LED array using flat LED modules.
Figure 5:
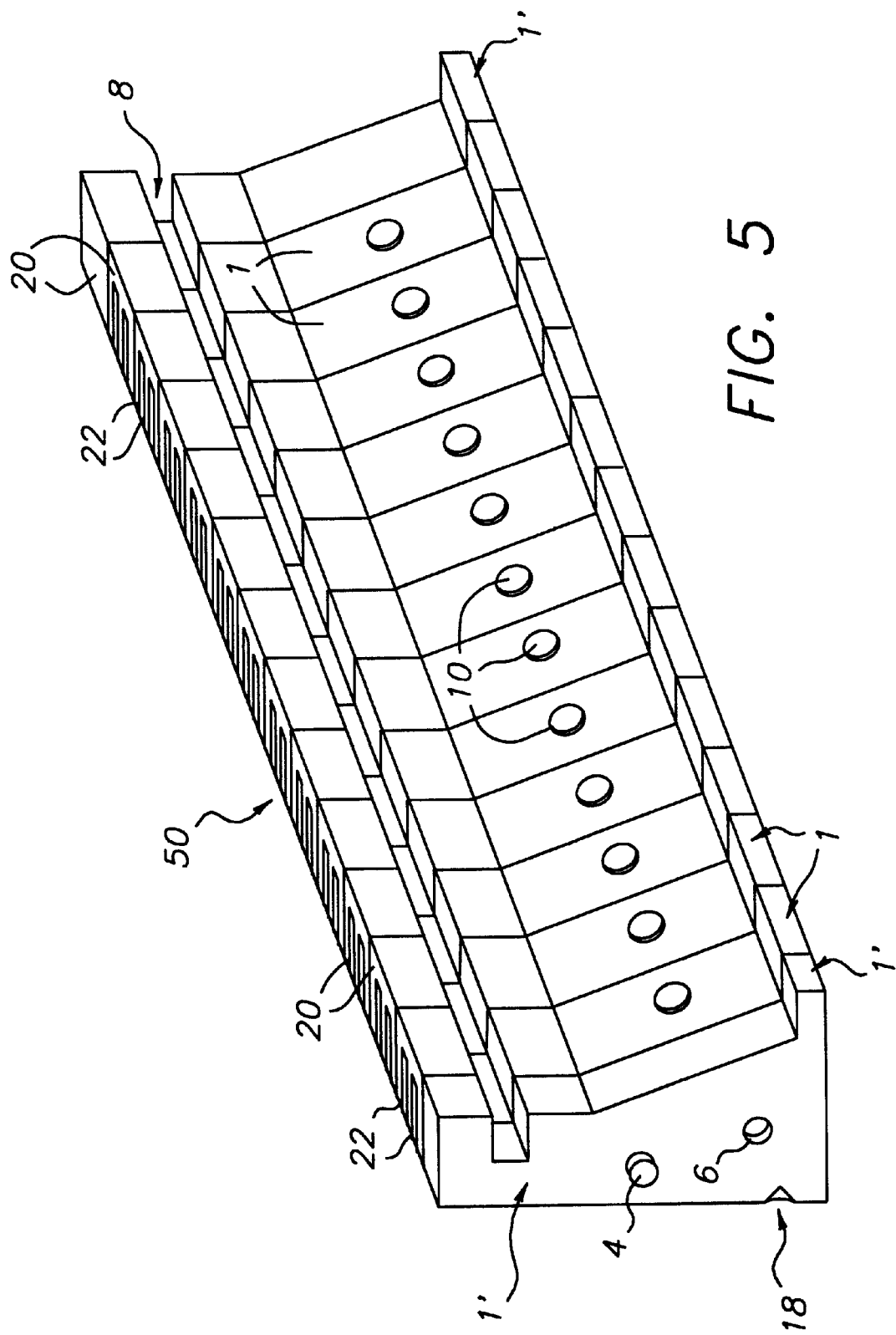
FIG. 5 is a perspective view of an LED array containing a plurality of LED modules of FIG. 1. This Figure also depicts a half width spacer module and a full width spacer module.

The housing 2 is made of any material that provides electrical insulation. It is preferred that the housing 2 be diffusely reflective at the wavelength(s) of interest. It is also preferred that the material be injection moldable with precision sufficient for making connective features such as the snaps 4 and 6. Although the snaps 4 and 6 (shown in FIGS. 1A and 1B) have a circular cross section, snaps with other cross sectional shapes may also be used. The sizes of the snaps 4 and 6 are of the order of one (1) millimeter, but could be made smaller or larger. Larger size snaps tend to be more robust. However, the size of the housing 2 limits the maximum size of the snaps. Thus, a larger housing is likely to have larger snaps. The snaps 4, 6 of adjacent LED modules 1 engage with one another and provide alignment and attachment of each LED module 1 to an adjacent LED module 1 (FIG. 2) forming an LED array. More specifically, the female snaps 6 of one LED module receive the male snaps 4 of an adjacent LED module when these LED modules are aligned. The attachment is provided via the locking action of the snaps 4 and 6. The snaps 4, 6 enable rapid assembly of one LED module to another. Other types of connective features may also be used. One such feature is described in a second embodiment of an LED module. The connective features of the LED modules allow these LED modules to be combined together (as shown in FIGS. 2, 3 and 4), providing an advantage of simple, inexpensive, custom LED arrays (FIG. 5). LED modules emitting different wavelengths are easily connected together providing a custom color balance.

At least one LED die 10 is mounted on surface 12 of the housing 2 of the LED module 1 (FIGS. 1A, 3, and 4). In this embodiment a single LED 10A is formed in the LED die 10. However, an LED die 10 may contain a plurality of LEDs. An LED module 1 may also contain more than one LED die 10. It is preferred that there be a reflective layer 11 (see FIG. 1A) between the LED die 10 and the surface 12 of the housing 2. This reflective layer 11 redirects the light (emitted by the LED towards the surface 12 of the housing 2) out of the LED module 1, maximizing the amount of usable light provided by the LED. If the LED produces visible wavelength light, a thin layer of Ag (silver) can be used for the reflective layer 11 because silver has a good reflectivity in the visible spectrum. A bonding wire 13 (preferably gold) is attached to the LED die 10 (FIG. 1A).

A first lead frame 14 extending from the base of the LED die 10 (or from the reflective layer 11, if this layer is electrically conductive) may be exposed along the lead frame surface 16 of the housing 2 (FIG. 1A). Another lead frame 14 is located next to the first lead frame and is attached to the bonding wire 13. This other LED frame may also be exposed along the lead frame surface 16 of the housing 2. The lead frames 14 are made of a conductive, ductile material (copper, for example) so that they can transmit electrical charge and can be bent around the surfaces of the housing 2 without fracturing. The exposure of the lead frames 14 to air provides a benefit in that heat generated by the operation of the LED die 10 may be rapidly conducted through the lead frames 14 and dissipated by air circulation. The LED module may also include an optional aperture snap 18 (not shown). The function of the aperture snap 18 is described in the "Integrating Cavity" section of this specification.

Surface 20 of the housing 2 of the LED module 1 provides support for two electrical connectors 22. These electrical connectors may be, for example, solder pads 22A, clips (not shown), connector pins (not shown), or ball grid array connectors (also not shown). Other electrical connectors may also be used. The electrical connectors are used to attach the LED modules 1 to a circuit board to make the required electrical connection to the circuit board.

Surface 24 of the housing 2, called the base surface, is located opposite the surface that supports the electrical connectors 22. One way to utilize surface 24 is described in the "Integrating Cavity" section of the specification.

Figure 6:
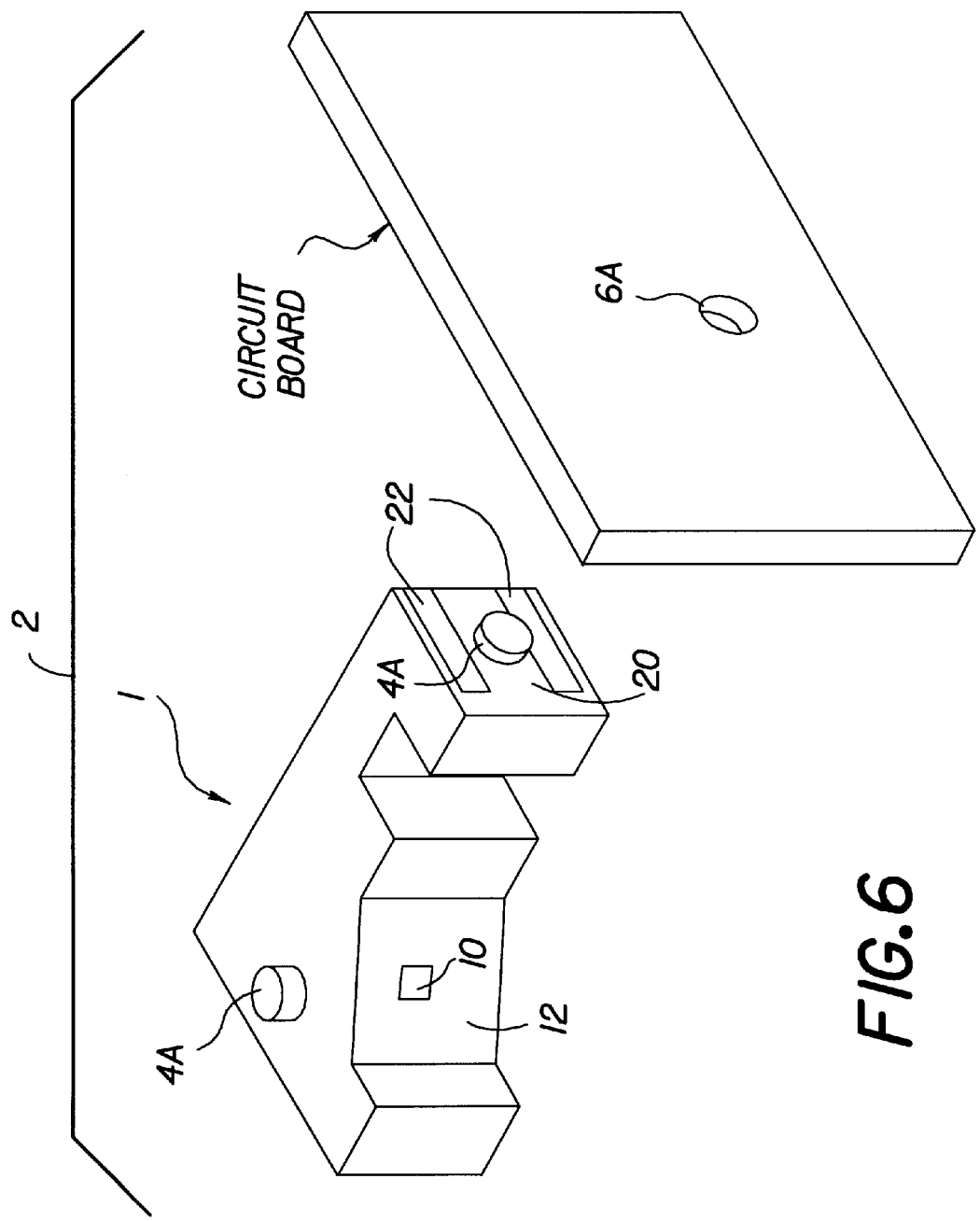
FIG. 6 shows an alternative form of an LED module with a protruding pin, and a circuit board with a complimentary socket for receiving the pin.

A second embodiment of an LED module 1 includes a housing 2 shown in FIG. 6. This LED module 1 incorporates a first connective feature in a form of at least one pin 4A protruding from the surface 20 of the LED module. A complimentary socket 6A is formed in a circuit board, so that as the LED module 1 is placed on the circuit board, the pin 4A engages the complimentary socket 6A of the circuit board, thereby locating the LED module on the circuit board with precision sufficient for the application. Further, additional (optional) pins 4A may be located on the sides of the housing 2 of the LED module and a complimentary connective feature in a form of a socket 6A may also be formed in this housing. The socket 6A and pins 4A of the adjacent LED modules may engage one another (not shown), forming an LED array that can then be placed on a circuit board. In this way, the LED modules are precisely located relative to the circuit board and with respect to one another. The attachment of one LED module to another LED module in this example is provided via friction. It may be required that no gaps be left between the LED modules. Thus, if the LED modules are not being attached to one another prior to being mounted on a circuit board, it would be preferred that the circuit board be constructed with the complimentary sockets spaced a distance equal to the LED module width. The pin 4A may be a plastic pin, injection molded on the LED housing. The sockets 6A may be holes precision drilled in the circuit board. If only one pin and one socket are used per LED module, and the pin and the socket are circular in cross section, the LED module may rotate around the pin's axis. Therefore, in order to control the rotational orientation of the LED module, it is preferable to utilize two pins and two sockets (of circular cross section) per LED module.

In addition to the LED modules 1, passive spacer modules 1' (i.e., modules without active LEDs) can be used to provide adjustable spacing between LED modules when forming custom LED arrays 50. The width of such spacer modules 1 may be larger, equal to, or smaller (½ or ¼, for example) than the width of the LED module 1. The spacer modules 1' are shown in FIG. 5.

It is preferred that the assembly of the LED arrays includes the following steps:

1.) Obtain a plurality of LED modules 1 and/or spacer modules 1' with connective features, and
2.) Connect LED modules and spacer modules (if needed) together in a predetermined order by engaging the connective features of the adjacent LED and/or spacer module(s), forming an LED array 50. This LED array 50 can then be attached or bonded to a circuit board.

Integrating Cavity

Figure 7A:
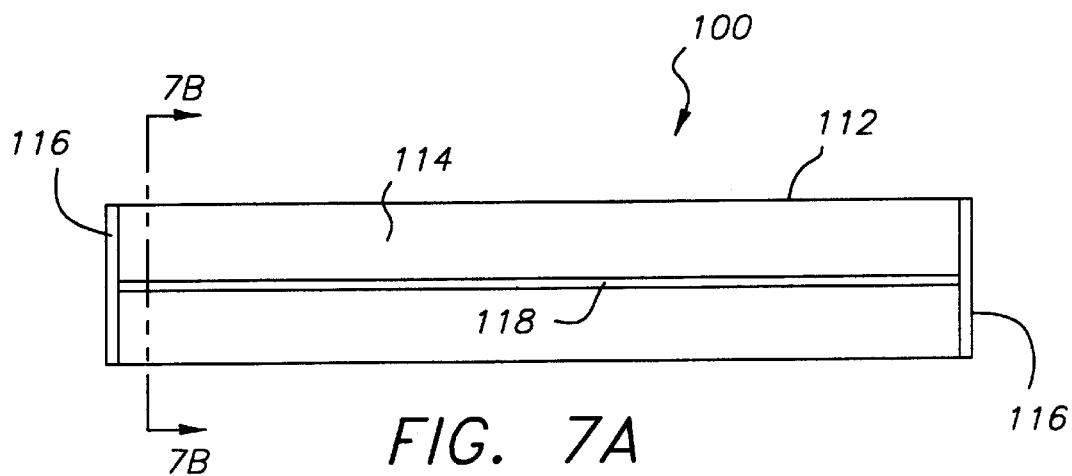
FIG. 7A is a plan view of one embodiment of an integrating cavity.
Figure 7B:
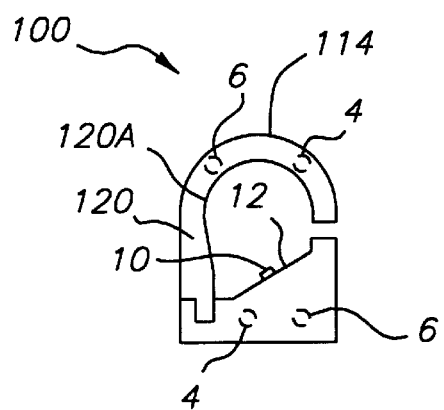
FIG. 7B is a cross section (taken along line 7—7) of an integrating cavity of FIG. 7A.
Figure 7C:
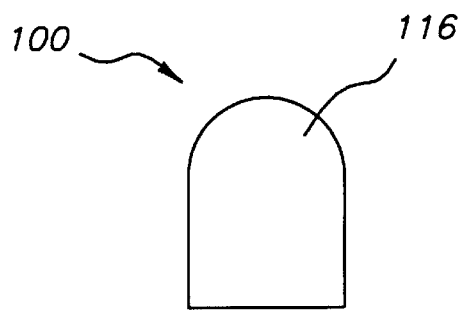
FIG. 7C is a side view of the integrating cavity of FIG. 7A.

An integrating cavity 100 (see FIGS. 7A–7C) includes, an integrating cavity housing 112 that comprises a tubular sidewall 114 extending between two end caps 116. The tubular side wall 114 may have an interior and exterior perimeters that are other than circular. The housing 112 has interior surfaces that are diffusely reflective with an overall reflectivity p of 90% to 99.99% and more preferably between 95% and 99.99%. The diffusely reflective interior surfaces of the housing 112 provide the integrating function of the integrating cavity 100. A narrow light exiting slit (in the tubular side wall 114) forms an exit port 118 of an integrating cavity. (However, the exit port 118 my have another shape, for example, a square shape described in detail later). The specific length and width of an exit port 118 depends on a particular application. The exit port 118 provides the only escape for the light trapped within the integrating cavity. A cavity 100 has a plurality of internal input ports formed by the LEDs. An input port is defined as a source of light that is being integrated by an integrating cavity. Thus, it may be in a form of a (back lit) hole or a slit that is used to illuminate an interior of an integrating cavity, or in a form of an LED or another light source mounted on an interior surface of the integrating cavity.

More particularly, as described earlier in the specification, the above described LED modules I may be used to form one or more LED arrays 50. These LED arrays 50 in combination with a reflective sheet 120 form an elongated tubular sidewall 114 of the integrating cavity 100 depicted in FIGS. 7A, 7B, and 8–14. Thus, the LEDs are mounted on interior surfaces of the integrating cavity, rather than in or adjacent to a slit or a plurality of holes in the housing walls. The height h of an integrating cavity 100 roughly equals the height h' of the LED modules 1 comprising these arrays (see FIGS. 9, 10 and 11). Since the physical size of the LED modules can be very small, use of an LED array to construct a side wall 114 of an integrating cavity housing results in an integrating cavity that is more compact than conventional integrating cavities. The resultant cavities 100 are highly efficient and provide uniform brightness at the exit port 118. More specifically, the optional slot 8 (see FIG. 1), may be formed in each LED module I of the LED array 50 to accept a thin reflective sheet 120 to enclose the integrating cavity 100 (FIGS. 8–14). Other mating features may also be used to connect the LED array(s) with the reflective sheet 120. FIGS. 9 and 10 illustrate that by changing the width L of the reflective sheet 120 one can change the separation between the two LED arrays 50, and thus change the size of the integrating cavity 100. If integrating cavity configuration is that of FIG. 10, changing the width L of the reflective sheet 120 will also change the width of the exit port 118. More specifically, the reflective sheet 120 has a diffusely reflective surface 120A. It is preferred that this reflective surface 120A has a reflectivity of 95% to 99.99%. The higher reflectivity values are preferred because they improve the efficiency of the integrating cavity.

Figure 8:
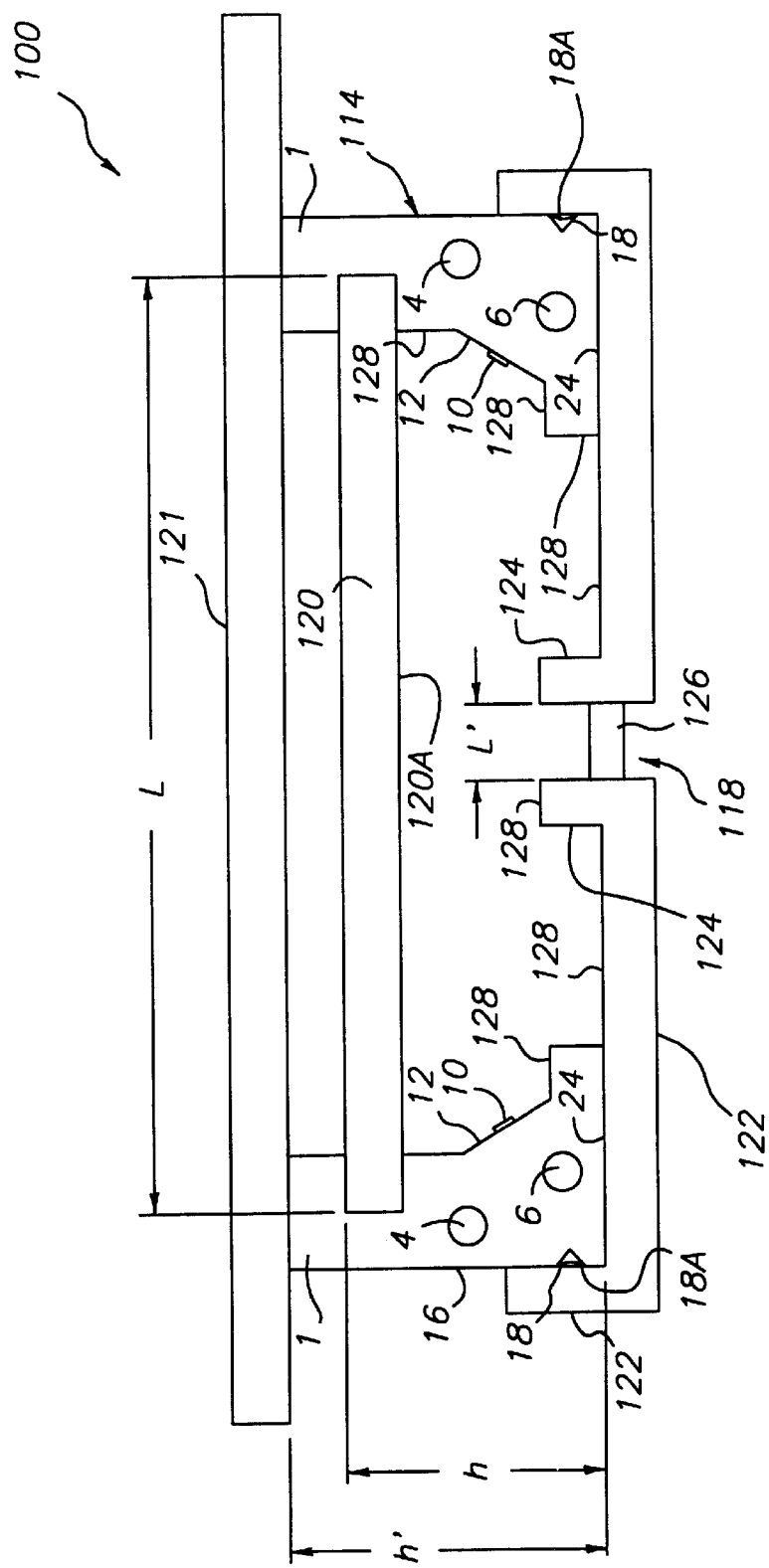
FIG. 8 is a cross sectional view of an integrating cavity constructed of LED modules of FIG. 1A.
Figure 9:
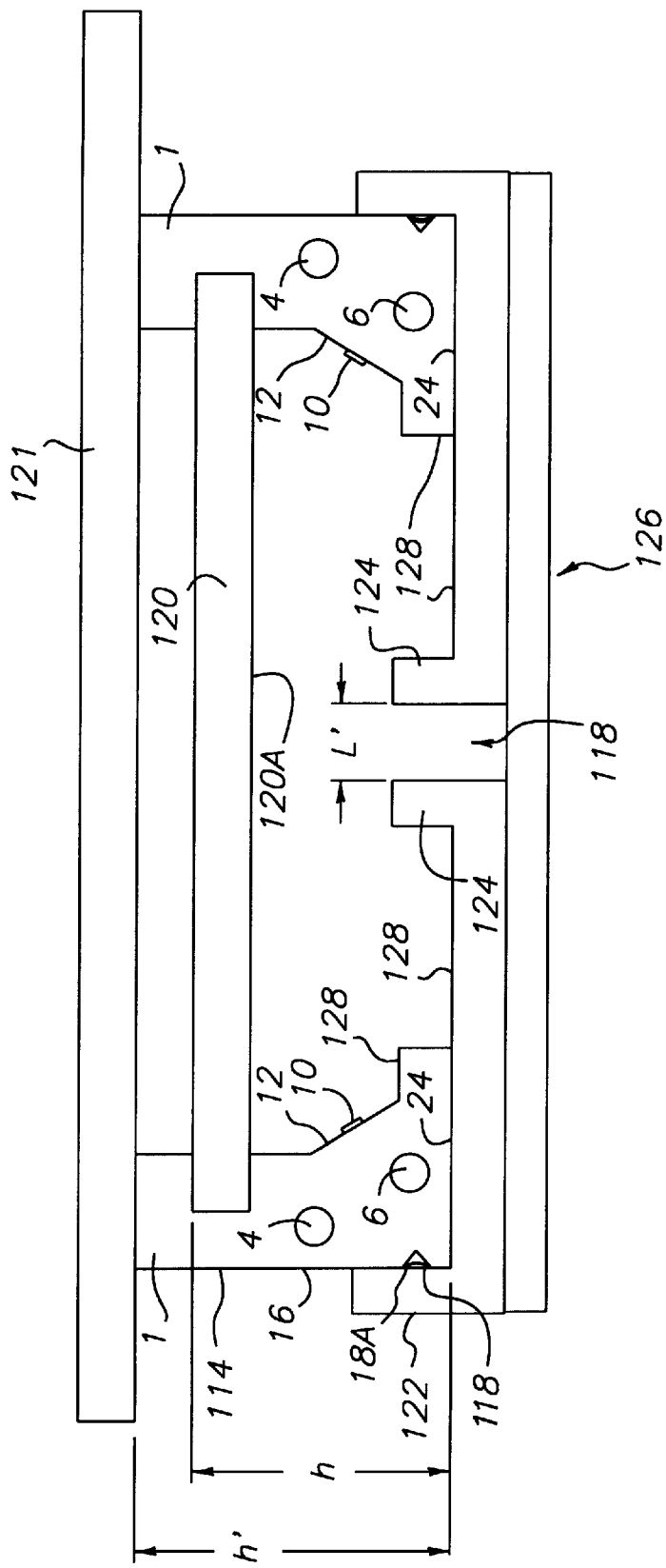
FIG. 9 is a cross sectional view of another integrating cavity.
Figure 10:
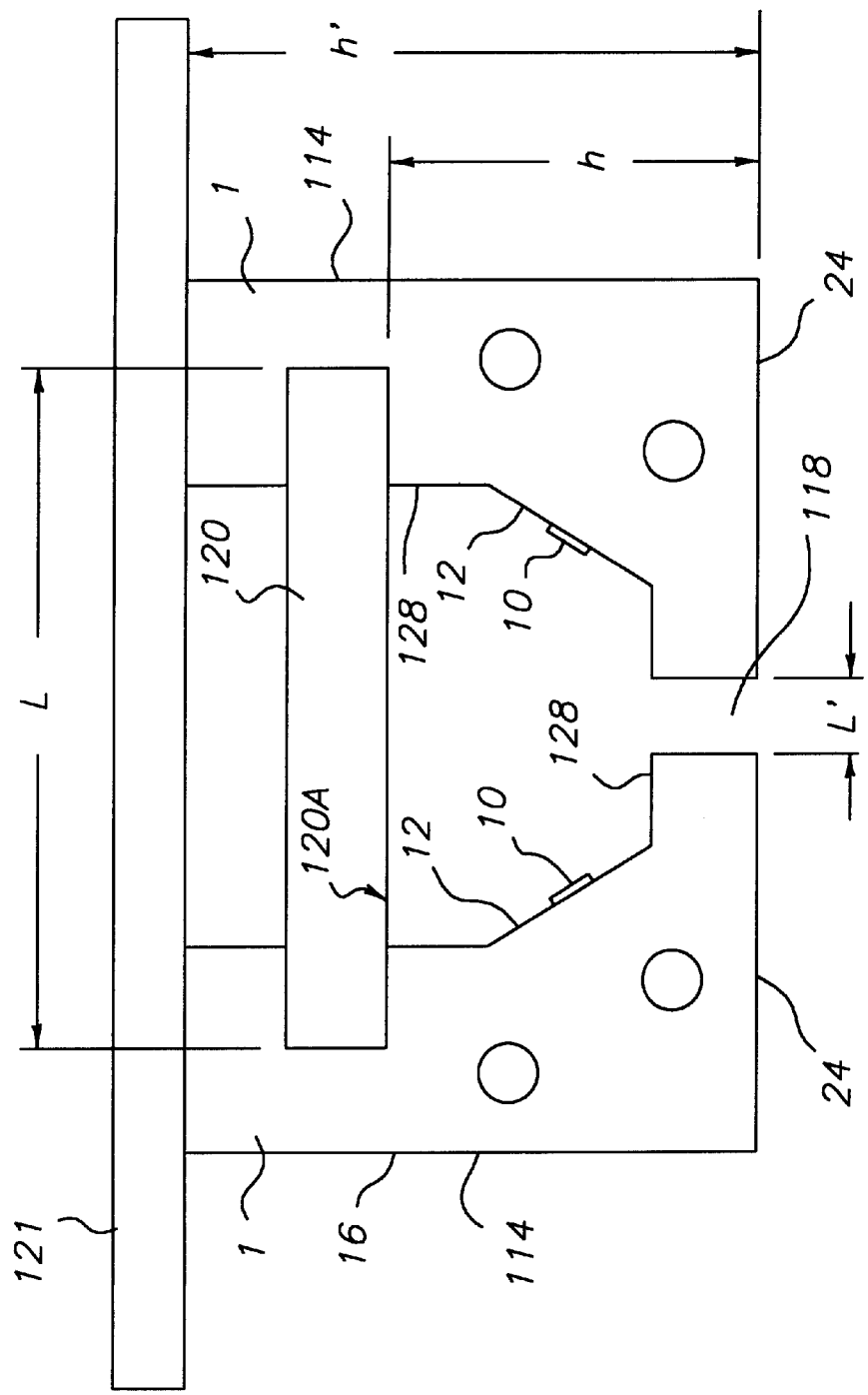
FIG. 10 is a cross sectional view of yet another integrating cavity, including a circuit board.
Figure 11:
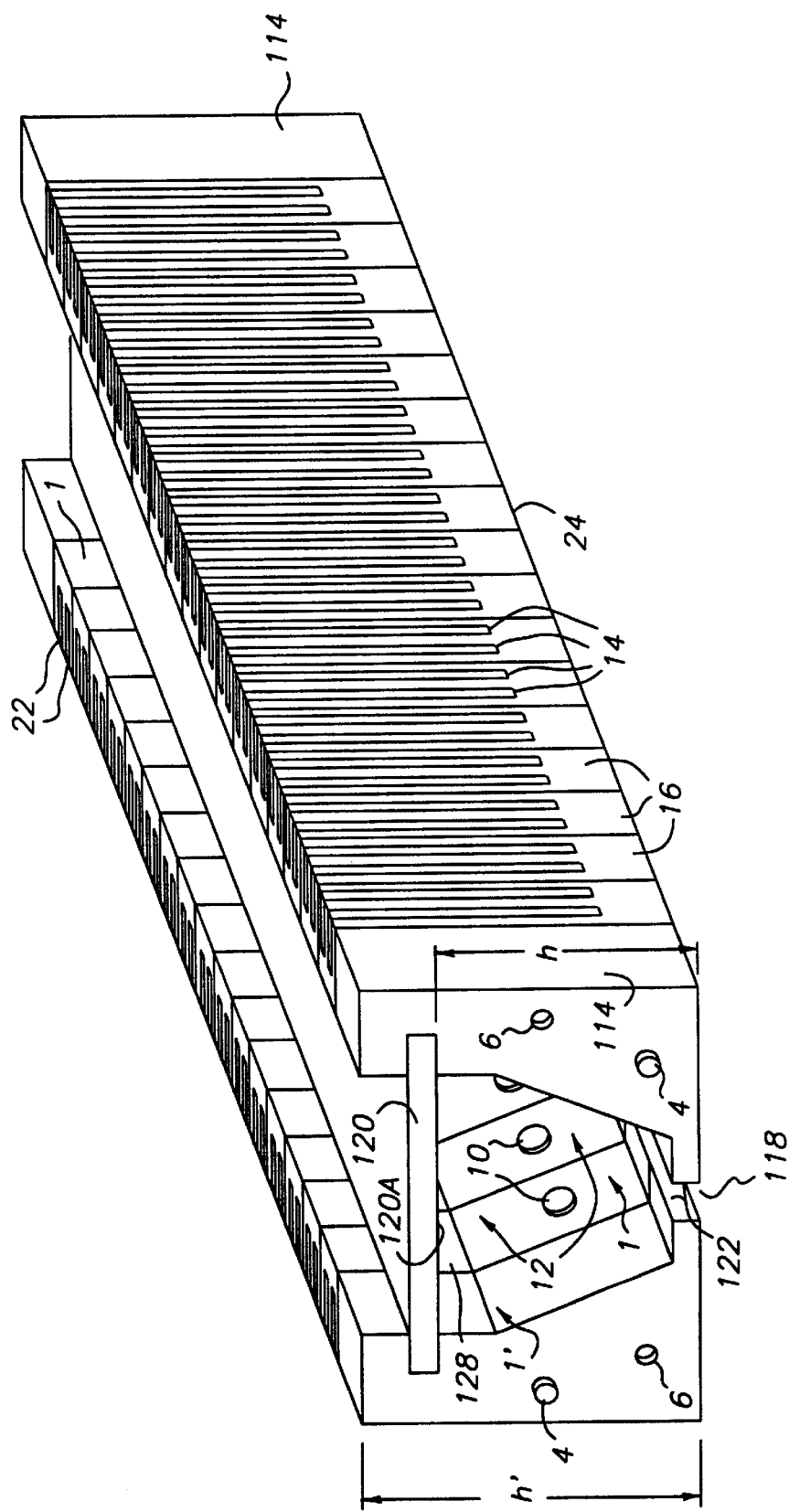
FIG. 11 is a perspective view of the integrating cavity of FIG. 10 without the circuit board and without end caps.
Figure 12:
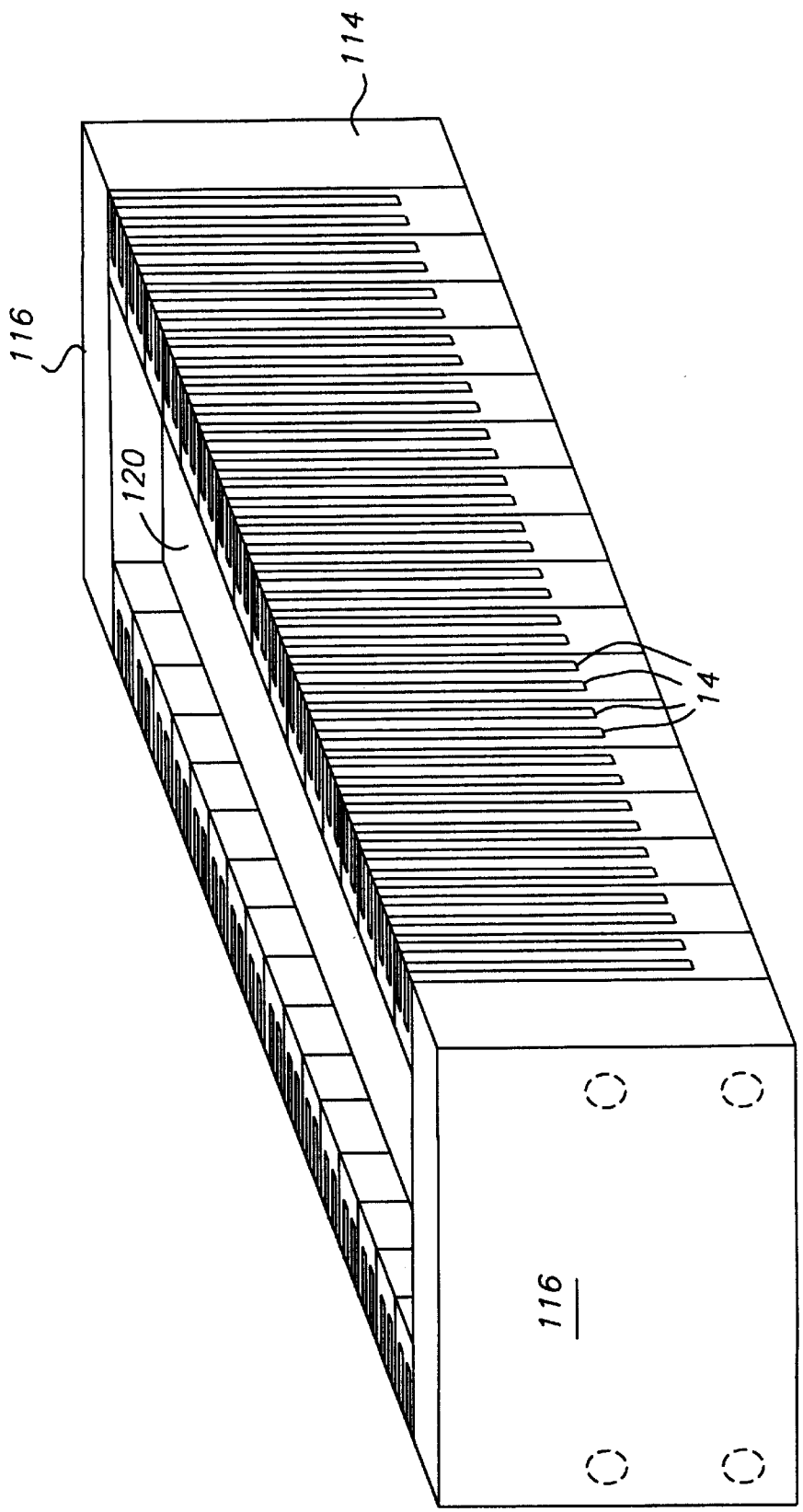
FIG. 12 shows the integrating cavity of FIG. 10 without the circuit board but with the end caps.
Figure 14:
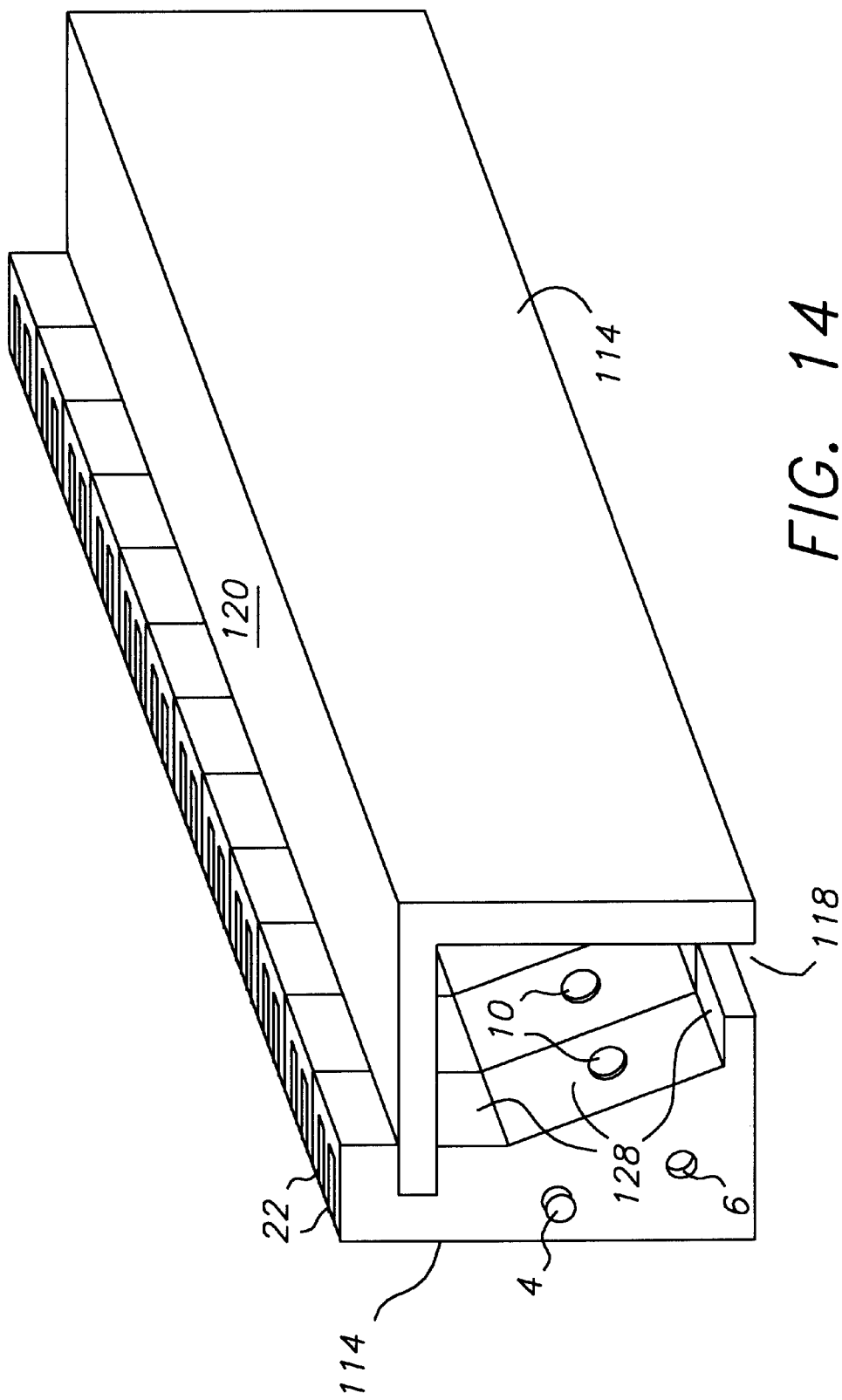
FIG. 14 is a perspective view of another integrating cavity.

FIGS. 8–10 show that the LED arrays forming side walls 114 are attached to a printed circuit board 121. The circuit board 121 is used to electrically drive the LEDs. FIGS. 11, 12, and 14 show integrating cavities prior to connection of the LED arrays to their respective circuit boards. As stated above, LED array(s) forming the tubular side walls 114 have a plurality of LEDs mounted on interior surfaces and emitting light towards interior surfaces of the integrated cavity. The following paragraph describes a preferred mounting arrangement for the LEDs.

As stated earlier in the specification, surfaces 12 of the LED modules 1 are LED mounting surfaces. These surfaces 12 can be made parallel to the LED frame surfaces 16 of the LED modules. However, LED modules must be configured such that the light emitted from the LEDs cannot escape the integrating cavity 100 without multiple reflections from the (diffusely reflective) interior surfaces of the integrating cavity. Thus, LEDs need to be facing away from the exit port 118 so that the light emitted from the LEDs does not directly exit the integrating cavity. If two LED arrays 50 are facing one another (as shown in FIGS. 8–10), it is preferred that the light emanating from one LED array does not directly impinge on the LED die 10 of another LED array. Thus, it is preferred that surfaces 12 be inclined surfaces facing upwards, i.e., toward the reflective sheet 120. (This is shown in FIGS. 8–11, and 14.) It is preferred that they be flat surfaces because it is easier to mount an LED die on a flat surface. It is also preferred that surfaces 12 be a diffusely reflective surfaces with a reflectivity of 90% to 99.99%. It is even more preferred that the reflectivity of surfaces 12 be in the 95% to 99.99% range. This is because surfaces 12 of LED modules in combination, comprise a large portion of the interior surface of the integrating cavity 100, and because low reflectivity values result in absorption of light by the interior surfaces, reducing integrating cavity efficiency. This is discussed in more detail in the "Performance Analysis" section of the specification.

Further, by having (i) LED dies mounted on the interior surfaces of the integrating cavity, and (ii) reflective layer 11 between the LED die and the surface 12 of the module, the efficiency of the integrating cavity is improved because all of the light provided by the LEDs reaches the interior of the integrating cavity. The additional goal of proper color balance for a given application of an integrating cavity can be achieved by intermixing LED modules of appropriate spectral content. For this purpose, LED dies of different spectral content may be obtained, for example, from Siemens Corp. located in Munich, Germany. Care must be taken to ensure: 1.) proper relative placement of the various color LED modules during LED array formation, and/or 2.) proper location of LED array(s) within the integrating cavity so that acceptable spectral mix and spectral uniformity are achieved. The optimum LED configuration can be achieved through either software modeling or building various integrating cavity configurations and evaluating their performance.

As stated earlier in the specification, an aperture snap 18 may be formed in the housing 2 of the LED modules 1 and/or spacer modules 1' (FIG. 8 and 9). The aperture snaps 18 (of the LED modules forming LED arrays) accept an optional mating snap 18A of an aperture frame 122, forming the exit port 118. The aperture frame 122 may include aperture baffles 124 as shown in FIG. 8. These aperture baffles 124 are optional and are configured to ensure that no radiation is emitted through the exit port 118 directly from the LEDs. Transmissive filters 126, such as diffusers or spectral trimming filters, can also be optionally added to the exit port 118 to modify the emitted light characteristics (see FIGS. 8 and 9).

Alternatively, a part of the integrating cavity housing 112 may form an aperture frame. This part of the integrating cavity housing may be welded or attached by other means to the bases 24 of the LED module 1. Also, an aperture frame (and thus, an exit port) may be formed by the bases 24 of the individual LED modules as shown in FIG. 10. Thus, each of the integrating cavities shown in FIGS. 7B and 8 through 14 have an exit port 118 formed by the aperture frame 122, bases 24, or an equivalent structure.

The end caps 116 are attached to the tubular side wall 114 (FIGS. 7A and 12) and may include optional connective features such as snaps 4 and 6. These connective features connect the end caps 116 to the LED array(s) 50 by engaging with corresponding connective features of the LED modules and/or spacer modules located at the edges of the LED array(s). Other ways of connecting the end caps 116 to the LED arrays are also possible. These include, but are not limited to, gluing or screwing the end caps to the tubular side wall 114. The end caps 116 have a diffusely reflective surface facing the interior of the integrating cavity and form a part of the integrating cavity housing 112.

Figure 13:
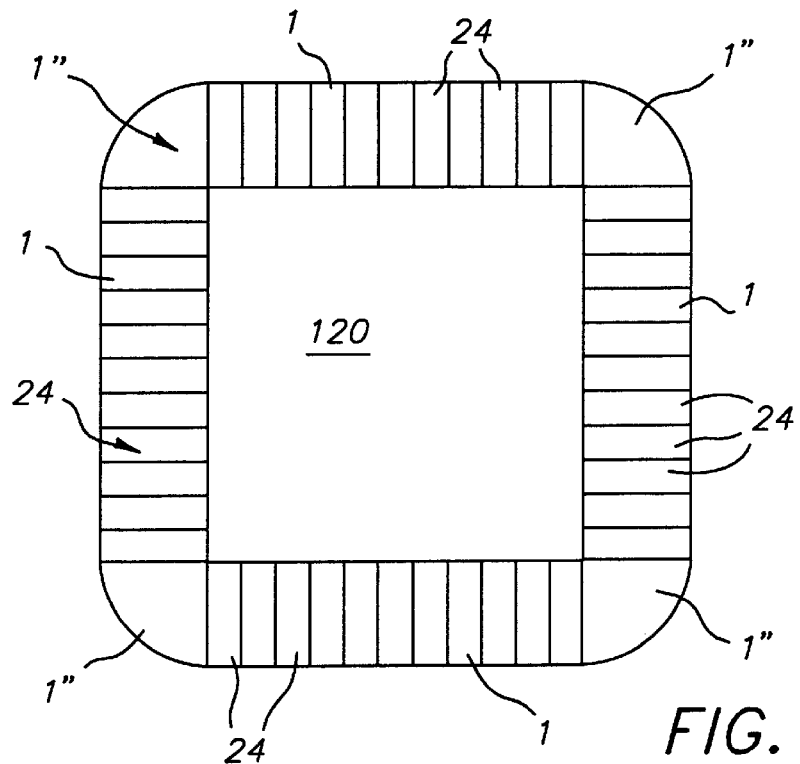
FIG. 13 is a bottom view of an integrating cavity with a square exit port.

Furthermore, corner modules 1" with snaps 4 and 6, and with optional aperture snap 18, and slot 8 (or a similar feature) may also be used to make an integrating cavity (see FIG. 13) with a brighter and/or wider exit port 118. More specifically, FIG. 13 is a bottom view through an exit port 118 of another integrating cavity that includes four LED arrays and four corner modules 100". The number of LED modules forming these LED arrays can be increased or decreased, changing the size and the shape of this integrating cavity. The size of the exit port 118 may be made smaller by attaching an aperture frame with a smaller exit port size (such as the aperture frame 122 described above) to the four LED arrays and the four corner modules. Transmissive filters, such as the filter 126, can also be optionally added to the exit port 118 to modify emitted light characteristics.

It is noted that conventionally formed LED arrays (comprising LED packages without the snaps) may also be used to form the housing 112 of an integrating cavity. However, the use of the modular LED arrays (i.e., LED arrays made of LED modules) in forming the integrating cavities allows for fast and inexpensive combination of various color LEDs in any sequence required by the spectral illumination needs of a specific application. In addition, the use of LED arrays with a slot allows for easy positioning of one LED array with respect to another LED array, or one LED array with respect to the rest of the integrating cavity housing. Thus, the reflective sheet 120 acts as a spacer, and together with the modular LED arrays 50 provides a simple and inexpensive way to construct an integrating cavity. The integrating cavity can be easily taken apart and its size changed by inserting a different size reflective sheet 120 into slots 8.

It is preferred that the assembly of an integrating cavity includes at least some of the following steps:

1.) Obtain a plurality of LED modules with snaps;
2.) Snap LED modules and spacer modules (as appropriate) together in a predetermined order by engaging the complimentary snaps of the adjacent LED and/or spacer module(s), thereby forming an LED array;
3.) Slide a reflective sheet of predetermined dimensions into slot 8;
4.) Attach end caps to the LED array(s);
5.) Attach or bond the LED array(s) to the circuit board.

Performance Analysis

Figure 15:
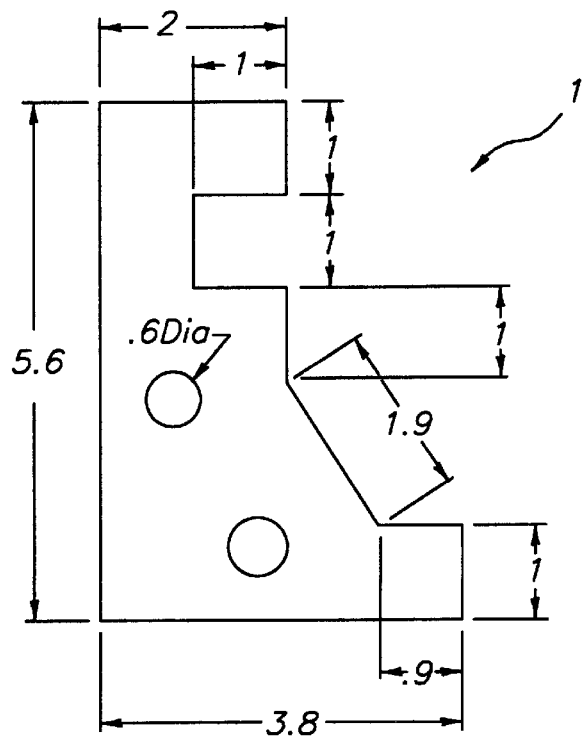
FIG. 15 is a cross sectional view of an LED module showing representative dimensions.

FIG. 15 depicts a cross sectional view of an exemplary LED module 1 (with specific dimensions provided in millimeters). Such modules have been utilized in modelling two LED arrays 50 that form a part of a tubular side wall 112 of the integrated cavity 100 used in the performance evaluation analysis described below. More specifically, the LED modules of FIG. 15 are arranged to form an integrating cavity, such as the one shown in FIG. 10 to illuminate an exit port 118 of 1 mm×24 mm. Each of the two LED arrays 50 utilizes twelve LED modules with LED centers separated by 2 millimeters. Thus, the length of the integrating cavity (without accounting for the thickness of the end caps) is 24 millimeters. For this analysis, all LEDs provide the same amount of light at the same wavelength ($\lambda$=550 nm).

The performance of any integrating cavity is characterized by efficiency $\epsilon$, brightness B, and brightness uniformity at exit port. Efficiency $\epsilon$ of an integrating cavity and brightness B at the exit port of the integrating cavity are determined by the ratio of four key parameters: the reflectivity of the internal surfaces of the integrating cavity (i.e., reflectivity of the inner walls 128), the input port area, the exit port area, and the total internal area of the integrating cavity. The efficiency $\epsilon$ is a ratio of the amount of the light exiting the integrating cavity to the amount of light entering the integrating cavity. More specifically, if the ratio of input port area to the exit port area is small (i.e., $A_{in}/A_{out}$=1/10 or less), the relationship of integrating cavity efficiency $\epsilon$ to the above four key parameters may be expressed by:

$$\varepsilon = \frac{\frac{(A_{in} + A_{out})\rho}{A_{cav}}}{1 - \rho\left[1 - \left(\frac{A_{in} + A_{out}}{A_{cav}}\right)\right]} = \frac{(A_{ratio})\rho}{1 - \rho[1 - A_{ratio}]}, \quad (1)$$

where $\rho$ is the reflectivity of the internal surfaces of the integrating cavity and often varies as a function of wavelength; $A_{out}$ is the total exit port area; $A_{in}$ is the total input port area; $A_{cav}$ is the total internal area of the integrating cavity (including the input and exit port areas $A_{in}$ and $A_{out}$); $A_{ratio}$ is the ratio of the total port areas ($A_{in}$ plus $A_{out}$) to the total internal area of the integrating cavity $A_{cav}$. Our model (i.e., the integrating cavity of FIG. 10) has a ratio of ($A_{in}$ plus $A_{out}$) to $A_{cav}$ of approximately 8%. When the reflectivity $\rho$ is 95%, this configuration results in an efficiency $\epsilon$ of approximately 63%. (This efficiency is approximately double that of the prior art integrating cavities). The reflectivity $\rho$=95% is possible with injection moldable materials, such as, for example, GE Valox™ available from General Electric Corp.

As shown in FIG. 10, LED dice 10 are mounted internally to the integrating cavity. Their surface area (input port area $A_{in}$) comprises only 0.5% of the total internal area of the integrating cavity $A_{cav}$ contributing to the high efficiency $\epsilon$. These LED dice 10 are commercially available from, for example, Siemens Corp., located in Munich, Germany. Other LED dice may also be used.

Figure 16:
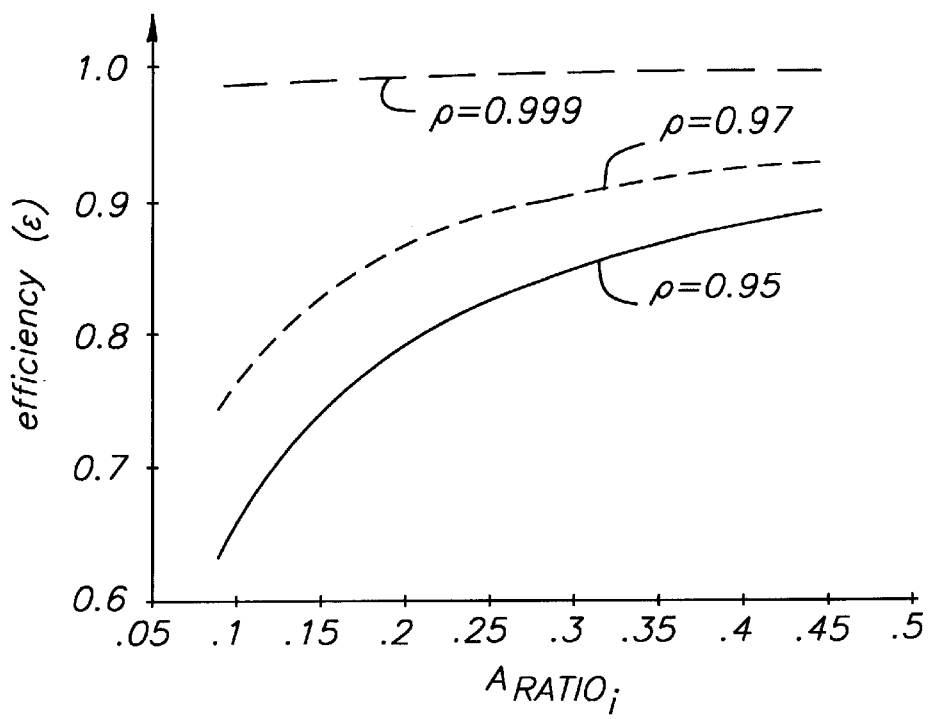
FIG. 16 is a plot of the integrating cavity efficiency with respect to the ratio of the exit port area to the total internal area of an integrating cavity.

Varying the quantity $A_{ratio}$ (i.e., the ratio of the total port area ($A_{in}$ plus $A_{out}$) to the total internal area ($A_{cav}$)) results in the range of efficiencies $\epsilon$ depicted in FIG. 16. To generate this graph the input port area $A_{in}$ was kept constant, and the width of the exit port was changed by moving apart the two LED arrays. This also increased the size of the integrating cavity resulting in a larger quantity $A_{cav}$. FIG. 16 illustrates that it is desirable to have a total port area ($A_{in}$ plus $A_{out}$) that is large with respect to the total internal area $A_{cav}$. Thus, for a given size total port area, it is preferred to have the smallest integrating cavity possible. Since $A_{in}$ is much smaller than $A_{out}$, and since only the quantity $A_{out}$ was increased, FIG. 16 implies that it is desirable to have:

1.) an exit port area $A_{out}$ that is relatively large, and
2.) a total internal area $A_{cav}$ that is relatively small.

It is preferred that the ratio of $A_{out}$ to $A_{cav}$ be larger than 0.03. It is more preferable that this ratio be larger than 0.04. It is even more preferable that this ratio be about 0.5 or higher. It is more preferable for this ratio to satisfy the following inequality:

$$0.05 \leq \frac{A_{out}}{A_{cav}} \leq 0.5.$$

The integrating cavity of FIG. 10 has a much smaller total internal area $A_{cav}$ than that of the prior art integrating cavities. The small size of this integrating cavity enables a large ratio of total port area to the total internal area, and thus, (for an integrating cavity with very small $A_{in}$) a large ratio of the exit port area to the total internal area (about 0.08). As stated above, this integrating cavity has a high efficiency of 63%. If the integrating cavity configuration shown in FIG. 14 is used, the resultant efficiency would be even higher because the total internal area of the integrating cavity is smaller than that of the integrating cavity of FIG. 10.

The efficiency $\epsilon$ of the integrating cavity is related to the relative brightness B of the exit port. More specifically, the relative brightness B is:

$$B = \epsilon / A_{out} \qquad (2)$$

Figure 17:
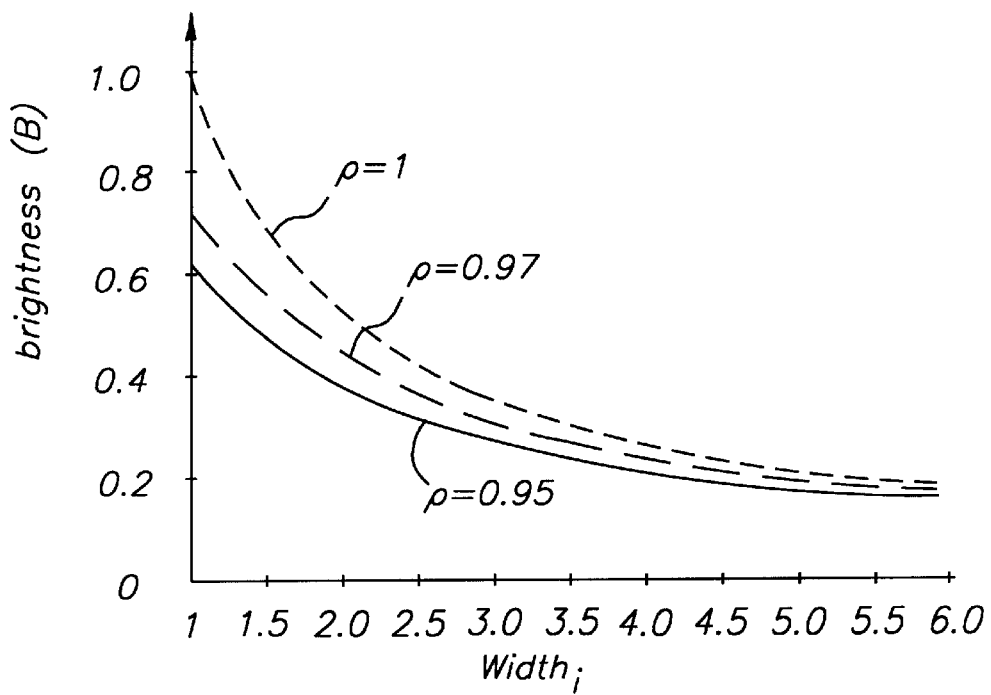
FIG. 17 is a plot of brightness at an exit port versus the exit port width for an integrating cavity of FIG. 10.

FIG. 17 depicts relative brightness of the integrating cavities of the type illustrated in FIG. 10. More specifically, the spacing L between the LED arrays (FIG. 9) was varied, resulting in a change of an exit port width L' and thus in the exit port area $A_{out}$. In addition, three values p were used, i.e., $\rho = 99.9\%$, 97%, and 95%. The resultant plot (FIG. 17) is a plot of brightness B versus output port width for the three reflectivity values $\rho$. The dashed line corresponds to $\rho = 99.9\%$, the dotted line corresponds to $\rho = 97\%$, and the solid line corresponds to $\rho = 95\%$. As shown in FIG. 17, for an exit port width of 1 mm and $\rho = 97\%$, a relative brightness of greater than 75% of the maximum theoretically possible brightness was achieved. The brightness equation (i.e., equation (2)) indicates that the size of the exit port is inversely proportional to brightness. Therefore, in order to have an integrating cavity with a high efficiency and a very bright exit port, it is preferable that $\rho > 95\%$, and that the following inequality be satisfied:

$$0.04 \leq \frac{A_{out}}{A_{cav}} \leq .02.$$

It is even more preferable that $\rho > 97\%$, and that $$.05 \leq \frac{A_{out}}{A_{cav}} \leq 0.15.$$

It is even more preferably that $\rho > 99\%$, and that $$.05 \leq \frac{A_{out}}{A_{cav}} \leq 0.12.$$

Figure 18:
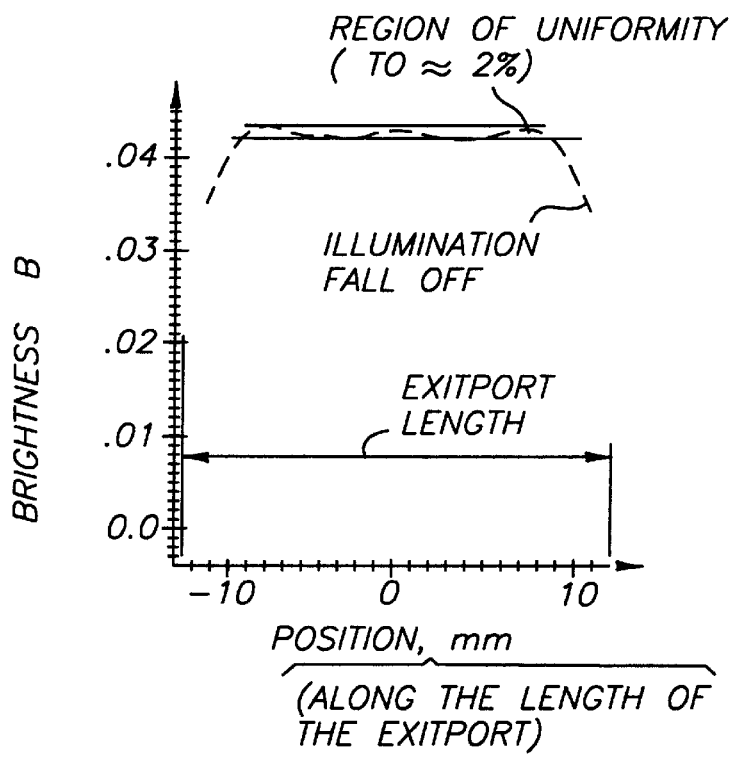
FIG. 18 is a plot of intensity across the length of the exit port of the integrating cavity of FIG. 10.
Figure 19:
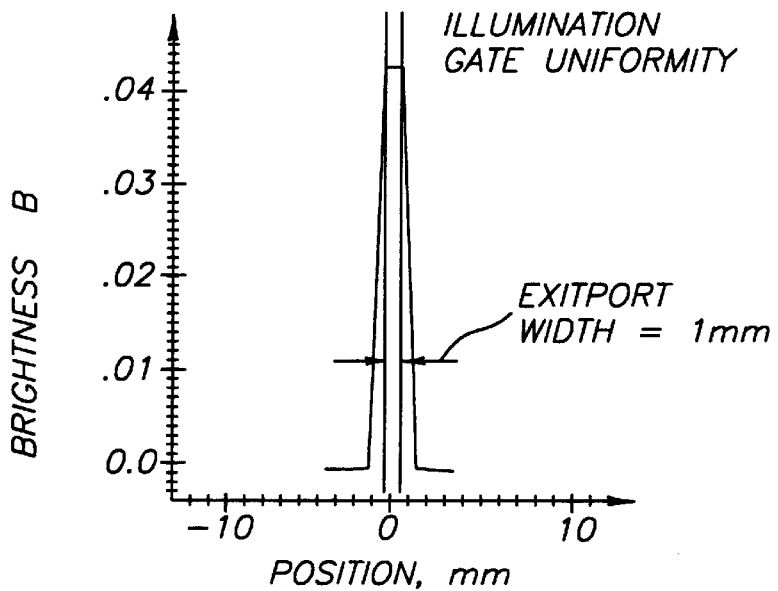
FIG. 19 is plot of intensity across the width of the exit port of the integrating cavity of FIG. 10.

The uniformity of radiation within the exit port has been modeled using a Monte Carlo ray tracing and energy evaluation software, Light Tools™. This program is commercially available from Optical Research Associates of Pasadena, Calif. Other software may also be used for this type of analysis. The results of this analysis (for the integrating cavity evaluated above) are shown in FIGS. 18 and 19. This analysis shows that there is adequate brightness uniformity for many applications. More specifically, FIG. 18 shows that the brightness is uniform (to within 2%) across most of the exit port length and falls off at the edges of the exit port. If greater uniformity is required across the length of the exit port, LEDs can be modulated as disclosed in U.S. Pat. No. 5,548,120 to compensate for the residual non-uniformity.

Further, FIG. 18 illustrates that because brightness falls off at the edges of the exit port 118, the exit port length should be longer than the length of the area to be illuminated. In this embodiment, an exit port 24 mm long provided a uniformly illuminated stripe that is about 17 mm long. If a 24 mm stripe needs to be illuminated uniformly, an integrating cavity with an exit port that is about 31 mm long can be constructed by simply adding 3 or 4 LED modules to each LED array. FIG. 19 illustrates that brightness is uniform across the entire exit port width and starts to fall off beyond the edges of the exit port.

The foregoing description of the invention is merely exemplary and minor changes and modifications to the invention as described are possible and wholly within the scope of the invention as set forth in the appended claims.

| PARTS LIST: | |
|---|---|
| 1 | LED module |
| 1' | spacer modules |
| 1" | corner modules |
| 2 | housing of the LED module |
| 4, 6 | male and female snaps |
| 4A | pin |
| 6A | socket |
| 8 | slot |
| 10A | LED |
| 10 | LED die |
| 11 | reflective surface |
| 12 | LED mounting surface |
| 13 | bonding wire |
| 14 | lead frame |
| 16 | lead frame surface |
| 18 | aperture snap |
| 18A | mating snap of the aperture frame |
| 20 | surface of housing supporting electrical connectors |
| 22 | electrical connectors |
| 22A | solder pads |
| 24 | base surface |
| 50 | LED array |
| 100 | integrating cavity |
| 112 | integrating cavity housing |
| 114 | tubular side wall |
| 116 | end caps |

-continued

PARTS LIST:

| | |
|---|---|
| 118 | exit port |
| 120 | reflecting sheet |
| 120A | reflective surface |
| 121 | printed circuit board |
| 122 | aperture frame |
| 124 | aperture baffle |
| 126 | transmissive filters |
| 128 | inner walls of an integrating cavity |

What is claimed is:

1. A light source device comprising:

a housing forming a light integrating cavity having a diffusely light reflective interior surface and an exit port;

at least one LED on said interior surface;

a light reflective layer and an electrically and thermally conductive layer between said LED and said housing;

electrical contact interconnecting said LED and the outside of said housing, such that electrical power applied to said electrical contact causes said LED to emit light.

2. A light source device according to claim 1 further comprising at least one LED array containing a plurality of LED dice, each of said plurality of LED dice containing at least one LED.

3. A light source device according to claim 2 wherein each one of said plurality of LED dice are on a flat surface.

4. A light source device according to claim 2 wherein said LED array contains LEDs of different wavelengths.

5. A light source device according to claim 1 wherein said housing comprises first and second portions, said portions having mating features such that said portions can be separated from one another, whereby one of said portions may be replaced by a similar portion of a different size.

6. A light source device according to claim 5 wherein said second portion of said housing is a diffusely reflective sheet.

7. A light source device according to claim 2 wherein said LED dice are on a tilted surface.

8. An integrating cavity comprising:

a housing with an exit port, said housing including (i) at least one input port LED array with a plurality of LEDs on a diffusely reflecting surface, said LED array forming a portion of a wall of said housing; and (ii) a diffusely reflective sheet attached to said LED array, said diffusely reflective sheet forming another portion of said wall; said integrating cavity having efficiency $\epsilon > 40\%$ and satisfies the following equations:

$$A_{in}/A_{out} < 0.1 \text{ and}$$

$$0.03 < A_{out}/A_{cav},$$

where $A_{in}$ is total input port area; $A_{out}$ is total exit port area; $A_{cav}$ is total internal area of the integrating cavity including input and exit port areas $A_{in}$ and $A_{out}$.

9. An integrating cavity according to claim 8 wherein $0.04 < A_{out}/A_{cav} < 0.2$.

10. An integrating cavity according to claim 8 wherein $0.05 < A_{out}/A_{cav} < 0.2$.

11. An integrating cavity according to claim 8 wherein $$0.05 < A_{out}/A_{cav} < 0.12.$$

12. An integrating cavity according to claim 8 wherein a cross section of said housing has a noncircular internal perimeter.

13. An integrating cavity according to claim 11 wherein said housing has a noncircular cross section.

14. An integrating cavity according to claim 9 further comprising diffusely reflective end caps.

15. An integrating cavity according to claim 9 wherein said LED array comprises LEDs of various wavelengths.

16. An integrating cavity according to claim 9 comprising two LED arrays facing one another, each of said two LED arrays having features adapted to engage said diffusely reflective sheet.

17. An integrating cavity according to claim 16 wherein said LED array is an LED array comprising a plurality of modules.

18. An integrating cavity according to claim 16 further comprising diffusely reflective end caps.

19. An integrating cavity according to claim 16 wherein a section of said LED arrays form said portion of said exit port.

20. An integrating cavity according to claim 16 wherein said LED arrays have LEDs mounted on surfaces that are inclined relatively to one another.

21. A light source device comprising:

a housing forming a cavity with a diffusely light reflective interior surface and an exit port;

at least one input port LED on said interior surface;

a light reflective layer and an electrically and thermally conductive layer between said LED and said housing;

electrical contact interconnecting said LED and the outside of said housing, such that electrical power applied to said electrical contact causes said LED to emit light, wherein the light source device has an efficiency $\epsilon > 40\%$ and satisfies the following equation:

$$0.04 < A_{out}/A_{cav},$$

where $A_{out}$ is total exit port area and $A_{cav}$ is total internal area of the cavity including input and exit port areas.

22. The light source device of claim 21 further comprising at least one LED array containing a plurality of LED dice, each of said plurality of LED dice containing at least one LED.

23. The light source device of claim 22 wherein said LED array contains LEDs of different wavelengths.

24. The light source device of claim 21 wherein said housing comprises first and second portions, said portions having mating features such that said portions can be separated from one another, whereby one of said portions may be replaced by a similar portion of a different size.

25. The light source device of claim 24 wherein said second portion of said housing is a diffusely reflective sheet.

* * * * *